(12) United States Patent
Derouet

(10) Patent No.: US 7,410,496 B2
(45) Date of Patent: Aug. 12, 2008

(54) ORTHOPEDIC IMPLANT CONSISTING OF A SUPPORT STRUCTURE PROVIDED WITH AT LEAST AN ORIFICE FOR PASSING THROUGH A FIXING SCREW ASSOCIATED WITH A NUT

(75) Inventor: Guillaume Derouet, Nantes (FR)

(73) Assignee: DLP, Saint-Herblain (FR)

( * ) Notice: Subject to any disclaimer, the term of this patent is extended or adjusted under 35 U.S.C. 154(b) by 182 days.

(21) Appl. No.: 10/496,395

(22) PCT Filed: Nov. 22, 2002

(86) PCT No.: PCT/FR02/04020

§ 371 (c)(1),
(2), (4) Date: May 24, 2004

(87) PCT Pub. No.: WO03/043513

PCT Pub. Date: May 30, 2003

(65) Prior Publication Data

US 2004/0267261 A1    Dec. 30, 2004

(30) Foreign Application Priority Data

Nov. 22, 2001  (FR) .................................. 01 15116

(51) Int. Cl.
*A61B 17/80* (2006.01)
(52) U.S. Cl. ..................................................... 606/290
(58) Field of Classification Search .................. 606/61, 606/69–71, 72, 73
See application file for complete search history.

(56) References Cited

U.S. PATENT DOCUMENTS

| | | | | |
|---|---|---|---|---|
| 2,580,821 A | * | 1/1952 | Nicola | 606/69 |
| 4,029,091 A | * | 6/1977 | von Bezold et al. | 606/69 |
| 4,484,570 A | * | 11/1984 | Sutter et al. | 606/72 |
| 5,234,431 A | * | 8/1993 | Keller | 606/70 |
| 5,269,784 A | | 12/1993 | Mast | |
| 5,380,325 A | * | 1/1995 | Lahille et al. | 606/61 |
| 5,545,228 A | * | 8/1996 | Kambin | 606/60 |
| 5,607,426 A | * | 3/1997 | Ralph et al. | 606/61 |
| 5,607,428 A | | 3/1997 | Lin | |

(Continued)

FOREIGN PATENT DOCUMENTS

WO       94/16634       8/1994

(Continued)

*Primary Examiner*—Eduardo C. Robert
*Assistant Examiner*—Richard Shaffer
(74) *Attorney, Agent, or Firm*—Young & Thompson

(57) ABSTRACT

An orthopedic device having a support structure provided with at least an orifice for a fixing screw associated with a nut; the head of the screw to be pressed on one side of the support, and the nut adapted to be pressed on the other side of the support, in a housing enabling its being integrated at least partly, so as to enable the support structure to be clamped between the screw head and the nut when the screw body has been completely screwed in the receiving bone material. The implantable device includes elements for maintaining the nut in its housing opposite the orifice, and elements for locking the nut in rotation. The contours of the housing and of the nut are dimensioned to provide at least one degree of freedom to the nut in the housing enabling self-centering of the screw and nut.

6 Claims, 5 Drawing Sheets

U.S. PATENT DOCUMENTS

| | | | |
|---|---|---|---|
| 5,728,127 A * | 3/1998 | Asher et al. | 606/61 |
| 5,964,761 A * | 10/1999 | Kambin | 606/61 |
| 6,030,389 A * | 2/2000 | Wagner et al. | 606/71 |
| 6,146,383 A * | 11/2000 | Studer et al. | 606/61 |
| 6,156,037 A * | 12/2000 | LeHuec et al. | 606/61 |
| 6,280,442 B1 * | 8/2001 | Barker et al. | 606/60 |
| 6,315,779 B1 * | 11/2001 | Morrison et al. | 606/69 |
| RE37,665 E * | 4/2002 | Ralph et al. | 606/61 |
| 6,641,583 B2 * | 11/2003 | Shluzas et al. | 606/61 |
| 6,663,632 B1 * | 12/2003 | Frigg | 606/69 |
| 6,695,846 B2 * | 2/2004 | Richelsoph et al. | 606/71 |
| 7,220,263 B2 * | 5/2007 | Cordaro | 606/69 |
| 2001/0014807 A1 * | 8/2001 | Wagner et al. | 606/61 |
| 2003/0045878 A1 * | 3/2003 | Petit et al. | 606/61 |

FOREIGN PATENT DOCUMENTS

| | | |
|---|---|---|
| WO | 99/09903 | 3/1999 |

\* cited by examiner

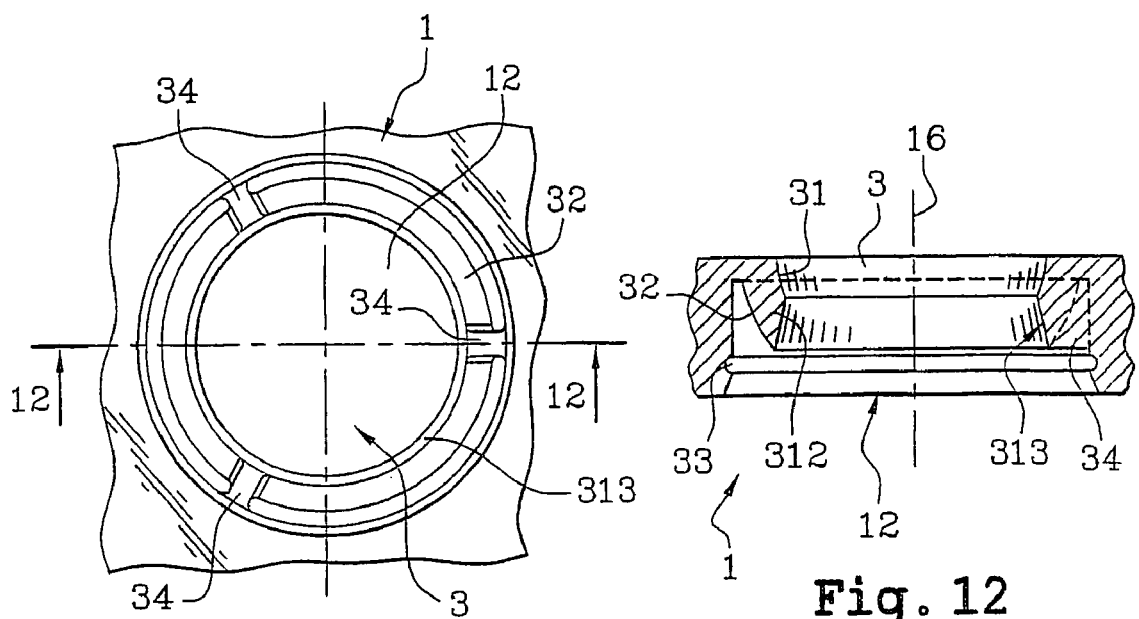
Fig. 11
Fig. 12
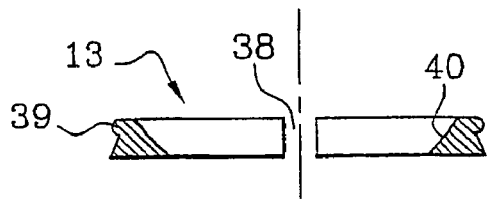
Fig. 19
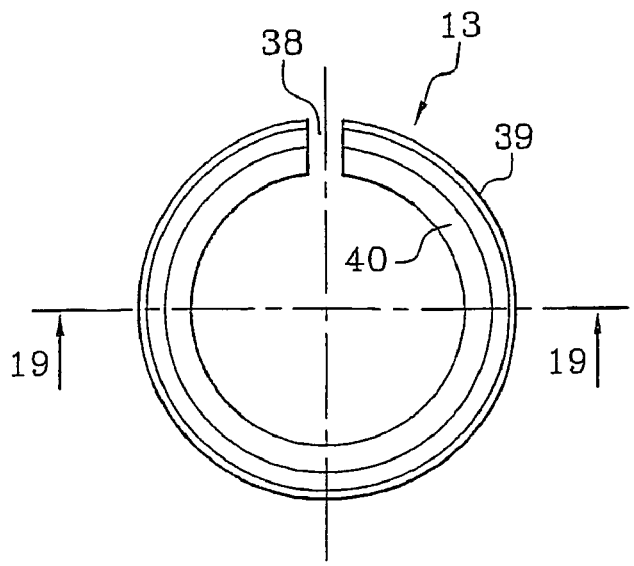
Fig. 18
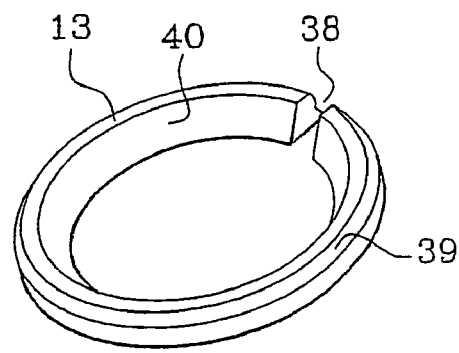
Fig. 17

ORTHOPEDIC IMPLANT CONSISTING OF A SUPPORT STRUCTURE PROVIDED WITH AT LEAST AN ORIFICE FOR PASSING THROUGH A FIXING SCREW ASSOCIATED WITH A NUT

BACKGROUND OF THE INVENTION

1. Summary of the Invention

The present invention relates to a new orthopaedic implant system of the type formed of a supporting structure fitted with at least one orifice to let through a fastening screw associated with a nut.

2. Description of the Related Art

Generally speaking, orthopaedic implants, in particular osteosynthesis implants, include a supporting structure in the form of a plate, a shell or other, fitted with one or of several orifices intended to let through fastening screw able of being anchored in the receiving bone material.

The general shape and the dimensions of this supporting structure are adapted to the implantation constraints.

There exist a very large number of types of implants which differ in particular by the presence or not of an interconnection between the screw head and the supporting structure, to optimise retention of the screw over a long period of time, and/or the presence of means conferring to the fastening screw a possibility of angular orientation relative to the axis of its reception orifice, to enable the practician position at best said screw relative to the site of implantation and to the corresponding spatial constraints.

Good holding quality of the implant is obtained when the supporting structure is sandwiched between the screw head and a nut, as known from the document WO-A-99/09903. But in such a case, the particular interconnection of the nut with the supporting structure requires accurate introduction of the fastening screw so as not to damage the thread of the nut during the screwing operation; and the practician has no possibility of orienting the screws spatially.

SUMMARY OF THE INVENTION

The present invention provides a new implantable orthopaedic device, simple in its structure, convenient, exhibiting good locking and holding qualities, and allowing certain possibility of spatial orientation of the fastening screw relative to the axis of the reception orifices laid out in the supporting structure.

This orthopaedic implant is of the type formed of a supporting structure fitted with at least one orifice to let through a fastening screw associated with a nut, the head of said screw being intended for resting on one side of said support, and said nut being intended for resting on the other side of said support, in a housing which enables at least partial integration, to allow clamping said supporting structure between the screw head and the nut, upon complete clamping of the screw body in the receiving bone material; this implantable device also includes means for holding said nut in its reception housing facing the orifice of the supporting structure, and for locking said nut in rotation.

According to the present invention, the contours of the housing of the supporting structure and the contours of the nut are sized to confer at least one degree of freedom to said nut in said housing, thereby enabling self-centring of the fastening screw and of the associated nut, regardless of the admissible orientation of the axis of said screw relative to the axis of the orifice of the supporting structure.

According to a first possible embodiment, the holding means of the nut in its reception housing are composed of a material rebound closing partially said housing.

According to another embodiment, these holding means are formed of an added-on clip closing partially the reception housing of nut.

In the latter embodiment, the clip for holding a nut is advantageously in the form of an open circular loop; this loop comprises a snap-on groove which co-operates with a throat of appropriate shape provided in the integration housing of the nut.

According to another characteristic, the means for locking the nut in rotation in the reception housing of the supporting structure are formed of at least one relief laid out on one of said parts (nut or supporting structure), co-operating with an adapted notch, provided on the other part (supporting structure or nut).

According to a particular embodiment, the implant includes cylindrical contact surfaces between the screw head and the supporting structure, on the one hand, and between the supporting structure and the nut, on the other hand. These cylindrical contact surfaces are adapted to confer to the fastening screw a possibility of orientation relative to the supporting structure, while keeping contacts between surfaces (cylindrical contacts) enabling to optimise the connection during clamping.

Preferably these cylindrical contact surfaces have the same axis.

According to a preferred embodiment, the implant includes spherical contact surfaces between the screw head and the supporting structure, on the one hand, and between the supporting structure and the nut, on the other hand, which are adapted to confer to the fastening screw a possibility of orientation relative to the supporting structure, while keeping contacts of surfaces (spherical contacts). This particularity confers important possibilities for angular adjustment of the screw and optimises the mechanic connection during clamping.

Preferably these spherical contact surfaces, in form of spherical caps have the same centre.

To obtain a compact assembly and having an interesting capacity of angular adjustment of the screws, the axis or the centre of the cylindrical or spherical contact surfaces, is situated in the vicinity of the upper plane of the supporting structure, or is confused with this plane.

According to still another particularity, the orthopaedic implant complying with the invention includes a nut containing a cylindrical shaft exhibiting a female thread and a spherical cap or crown situated at the periphery of said cylindrical shaft.

According to still another particularity, the fastening screw is fitted with a body thread able to co-operate with the receiving bone material, and of a head thread able to co-operate with the associated nut, the outer diameter of the body thread being smaller than or equal to the outer diameter of the head thread to let the screw through the nut.

For optimised clamping, the fastening screw(s) are advantageously fitted with a head thread composed of n threads offset by 1/n turns, and whereof the pitch co-operates with that of the thread of the nut and to that of the body thread.

BRIEF DESCRIPTION OF THE DRAWINGS

The invention will be further illustrated, without being limited thereto, by the following description of several particular embodiments, given solely for exemplification purposes and represented on the appended drawings whereon:

FIG. 11 is a large-scale partial view, of the underside of the supporting structure showing the reception housing of the nut;

FIG. 12 is a sectional view according to 12-12 of FIG. 11;

FIG. 17 is a large-scale perspective view of the circular clip enabling to hold the nut in the housing of the supporting structure;

FIG. 18 is a top view of the clip illustrated on FIG. 17;

FIG. 19 is a diametrically sectional view of the clip according to 19-19 of FIG. 18.

DESCRIPTION OF THE PREFERRED EMBODIMENT

Figure 1:
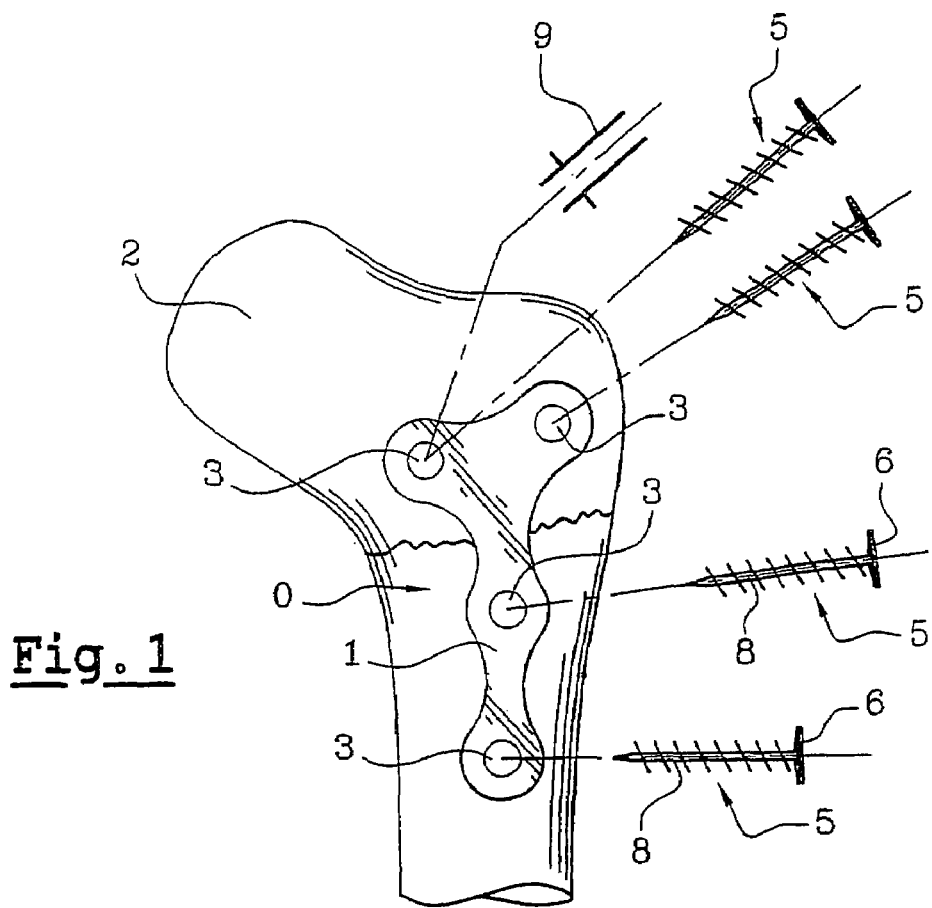
FIG. 1 represents generally an orthopaedic plate positioned at the surface of a fractured bone, and intended to receive fastening screws.

FIG. 1 shows the orthopaedic implant 0 formed of a supporting structure in the form of an osteosynthesis plate 1 positioned on a fractured bone 2, for example, an epiphysis of the radius, and exhibiting four circular orifices 3 for accommodating the fastening screws 5. Each screw 5 includes a screw head 6 and a screw body 8.

FIG. 1 also illustrates the drilling gun 9 which is used before placing the screws 5 in order to drill positioning holes in the bone material, through the orifices 3.

Figure 2:
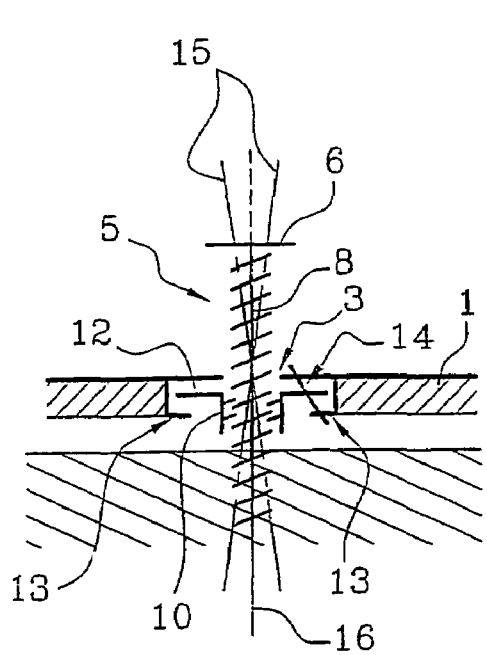
FIG. 2 is a functional flow chart of a first possible embodiment of an implant of the present invention.

FIG. 2 is a functional flow chart which shows schematically the assembly of a screw 5 on the supporting plate 1.

On this figure, one may note the presence of un nut 10 positioned in a housing 12 laid out in the supporting plate 1, so that upon complete screwing of said plate 1 is sandwiched between the head 6 of the screw 5 and said nut 10. The female thread of the nut 10 co-operates with the male thread of the screw body 8 to lock the assembly upon complete screwing.

To this end, the screw 5 may include a single thread, on the one hand for anchoring in the bone material, and on the other hand for co-operation with the nut; but it may also be fitted with two different threads each ensuring one of the functions aforementioned.

The nut 10 may be simply integrated partially in the housing 12. It is held in place in said housing 12, facing the orifice 3, by appropriate holding means 13, and it is also locked in rotation by appropriate means represented in the form of a simple line marked 14.

The holding means 13 may be in the form of a material rebound or of an added-on structure detailed below, of the locking clip type, implemented, after positioning the nut 10 in the housing 12.

The rotation of the nut 10 is locked either by the general relative shapes of the nut 10 and of the reception housing 12, or by co-operation of complementary members such as relief (s) and notch(es), laid out on the surfaces facing the nut and of the housing.

According to the invention, the contours of the housing 12 and the contours of the nut 10 are adapted and sized to confer to the latter, in said housing, at least one degree of freedom, greater than that of a simple functional clearance, thereby enabling self-centring of the screw 5 and of the nut 10, and this regardless of the admissible orientation of the axis of said screw relative to the axis of the housing 3.

FIG. 2 shows both lines of axes 15 illustrating the amplitude of possible corresponding inclinations of the screws. The middle position, normal to the supporting plate 1 is represented by the axis 16, which axis 16 corresponds to the axis of the housing 3.

Figure 3:
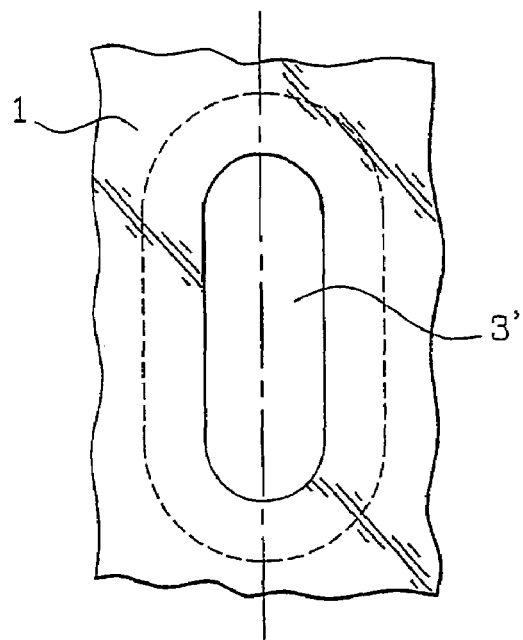
FIG. 3 illustrates a top view of a possible embodiment of an orifice laid out in the supporting structure to let through a fastening screw.

As represented on FIG. 3, the supporting plate 1 may include elongated orifices 3' thereby giving a possibility of additional longitudinal adjustment of the screws 5 with respect to the support 1. These elongated orifices 3' may have a general rectilinear or curvilinear shape.

FIGS. 4, 5, 6 and 7 are functional diagrams derived from that of FIG. 2, illustrating the screwed assembly of the invention, but with cylindrical or spherical contact surfaces between the screw head 6 and the supporting plate 1, on the one hand, and between the supporting plate 1 and the nut 10, on the other hand, authorising a degree of freedom and relatively important angular adjustment possibilities of the screw 5, while keeping a significant contact surface promoting good cohesion of the assembly after screwing.

In all cases, the different parts are shaped as well as possible to obtain significant angular adjustment possibilities and to keep the best possible contacts between surfaces. In the case of cylindrical contact surfaces, the angular adjustment is possible in a plane if the orifice 3 is circular, or in different parallel planes corresponding to a prismatic volume if an oblong orifice 3' as illustrated on FIG. 3 is available.

In the case of spherical contact surfaces, there is preferably a circular reception orifice and the angular adjustment of the screw is then possible within a conical volume whereof the axis is confused with that of the circular orifice 3.

Figure 4:
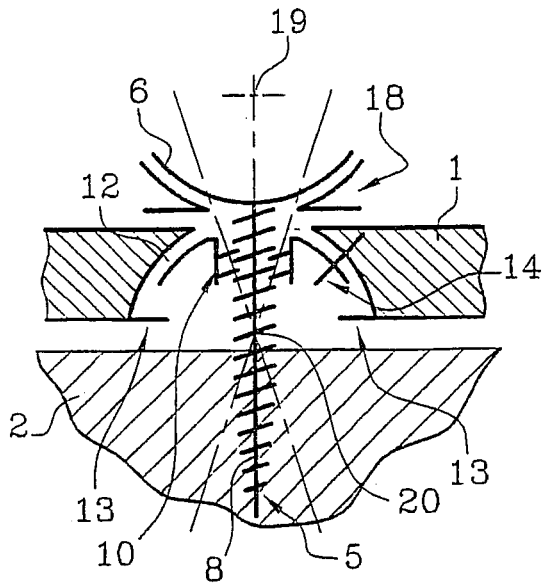
FIGS. 4 to 7 illustrate four different functional flow charts of implants of the present invention, authorising angular adjustments of the axis of the screw relative to the supporting structure.

On FIG. 4, the head 6 of the screw 5 is en contact with an intermediate member 18 which comprises a slipping surface in contact with the supporting plate 1. The contact surfaces between the head 6 and this added-on member 18 correspond to a cylindrical portion centred on an axis 19, or to a spherical cap centred at a point 19, as the case may be. The axis or the centre 19 is here positioned on the outside, above the supporting plate 1.

On the other hand, the nut 10 and the supporting plate 1 are also in contact on cylindrical or spherical surfaces, as the case may be. The axis or the centre 20 of the cylindrical portion or of the corresponding portion of spherical cap is here positioned on the inside, i.e. on the bone structure side.

The nut 10 is held in place by the means 13 and it is locked in rotation by means 14 schematised in the form of a simple line.

Figure 5:
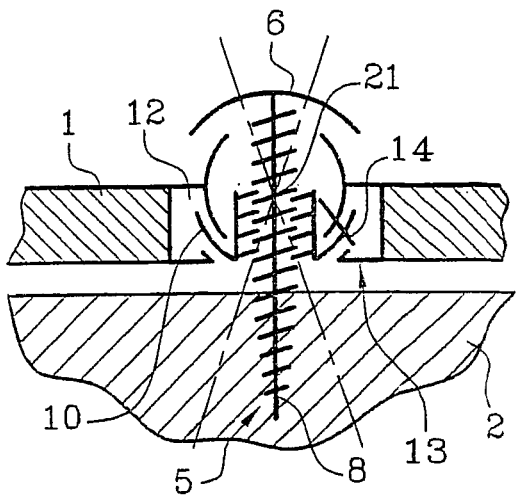
Figure 6:
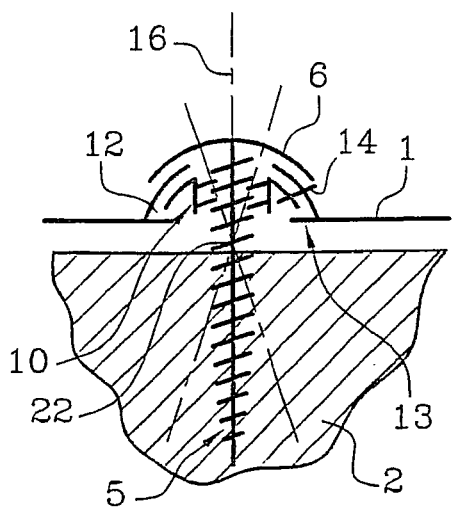
Figure 7:
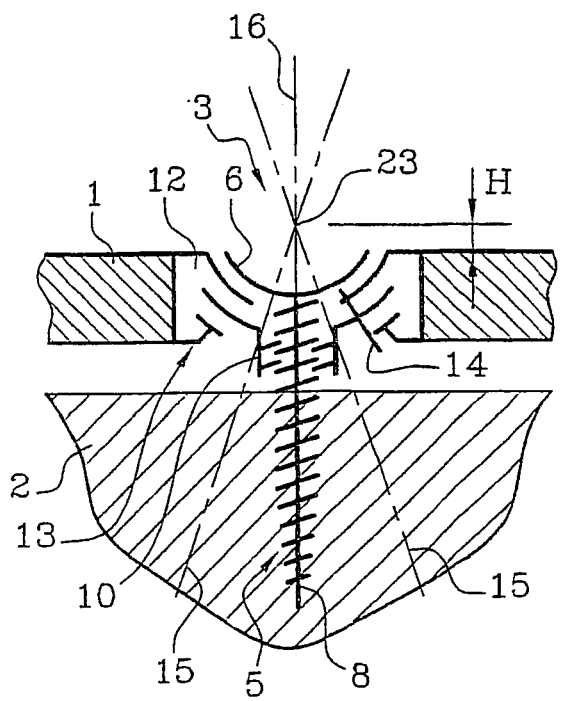

FIGS. 5, 6 and 7 illustrate embodiments deprived of complementary part 18 and whereof the spherical or cylindrical contact surfaces of the screw/supporting plate and supporting plate/nut are centred on the same axis or exhibit the same centre.

For the embodiment illustrated on FIG. 5, the axis or the corresponding centre 21 is situated between both contact surfaces.

For the embodiment illustrated on FIG. 6, the axis or the corresponding centre 22 is situated on the inner face of the supporting structure 1.

For the embodiment of FIG. 7, the axis or the corresponding centre 23 is situated on the outer face of the supporting structure 1.

The embodiment illustrated on FIG. 7 appears more compact. Preferably, the axis or the centre 23 is situated in the vicinity of the upper surface of the supporting structure 1 to enhance the possibilities of angular bottoming of the screw 5; the distance marked H on this figure tends then towards zero value.

In all cases, the nut 10 is held in its housing 12 by means 13 such as material rebound or clip as detailed below, and it is locked in rotation by means represented schematically in the form of a simple line 14 also detailed below.

Because of the general space requirements of the parts, the corresponding angular clearance cone always confers to the practician interesting adjustment possibilities.

FIGS. 8 to 19 detail an embodiment according to that represented diagrammatically on FIG. 7.

Figure 8:
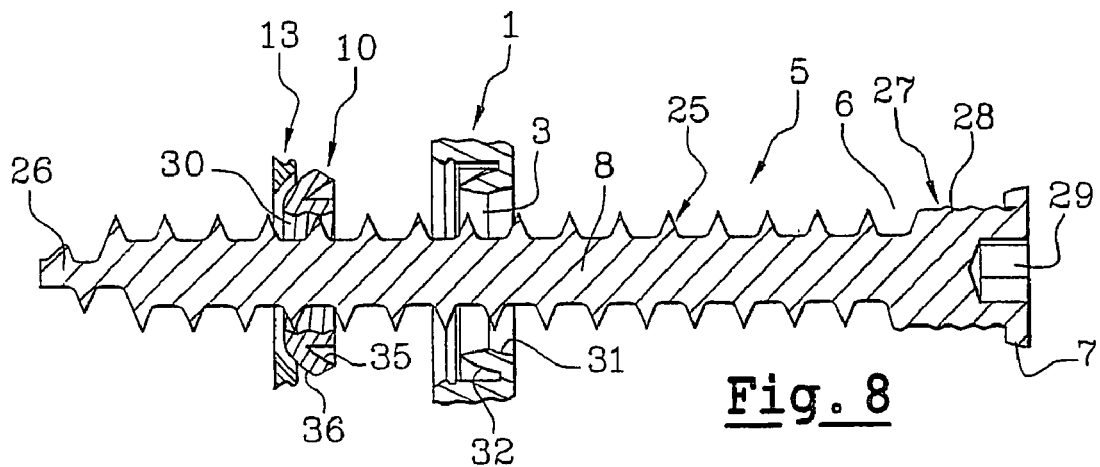
FIG. 8 is an exploded sectional view, of a preferred embodiment of implant of the functional flow chart of FIG. 7.

FIG. 8 represents a fastening screw 5 as a longitudinal diagrammatical section. This screw 5 shows on the one hand a screw body 8 fitted with a thread 25 and whereof the end 26 is pigtail-shaped, and on the other hand a screw head 6 fitted with one clean thread 27. The upper section of the screw head 6 contains a cavity 29 with polygonal walls co-operating with the setting auxiliary device.

This screw head 6 shows at its end a collar whereof the peripheral contour is in the form of a spherical crown 7, intended to make contact with a surface of equivalent shape provided on the supporting structure 1.

The screw 5 runs through the plate 1, seen as a sectional view, at the circular orifice 3, as well as the nut 10 and the holding means 13, here in the form of a locking clip, also seen as a sectional view.

The supporting structure 1, the nut 10 and the locking clip 13 are represented in exploded views, separate from one another.

The thread 27 of the screw head 5 is adapted to that of the nut 10. This thread is composed of n threads 28 offset by 1/n turn, whereof the pitch is able to co-operate with that of the thread 30 of the nut 10, which pitch corresponds to that of the thread 25 of the screw body 8.

The thread 25 of the screw body 8 may be anchored by screwing in the bone material; the outer diameter of this body thread 25 is smaller than or equal to the outer diameter of the head thread 27 to let the screw body 8 through the threaded orifice of the nut 10.

Figure 9:
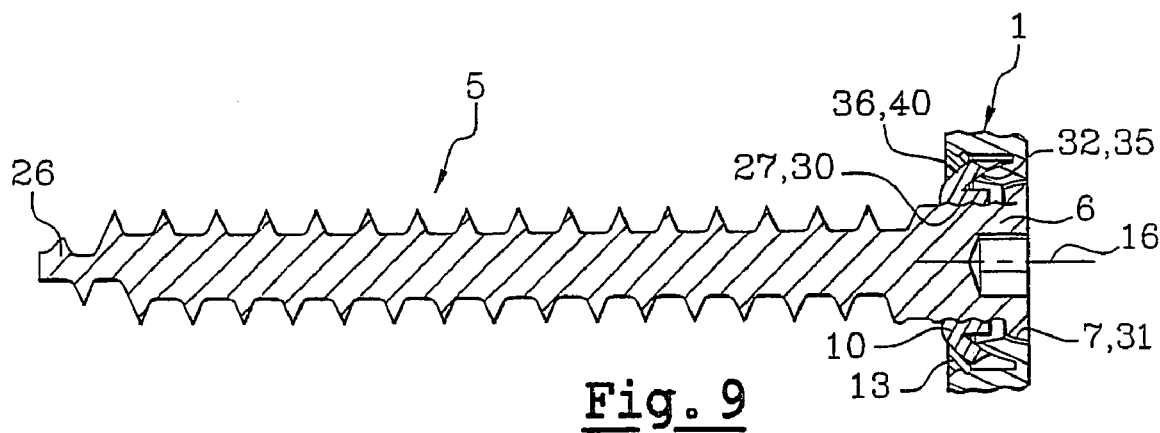
FIG. 9 shows the implant of FIG. 8, upon complete straight screwing, i.e. the screw is centred on the axis of the orifice of the support.

FIG. 9 represents the fastening screw 5 upon complete screwing, in a configuration normal to the plate 1 (the bone reception structure is not represented). The plate 1 is then sandwiched between on the one hand the screw head 6, and on the other hand the nut 10 whereof the female thread 30 co-operates with the male thread 27 of said screw head 6.

Figure 10:
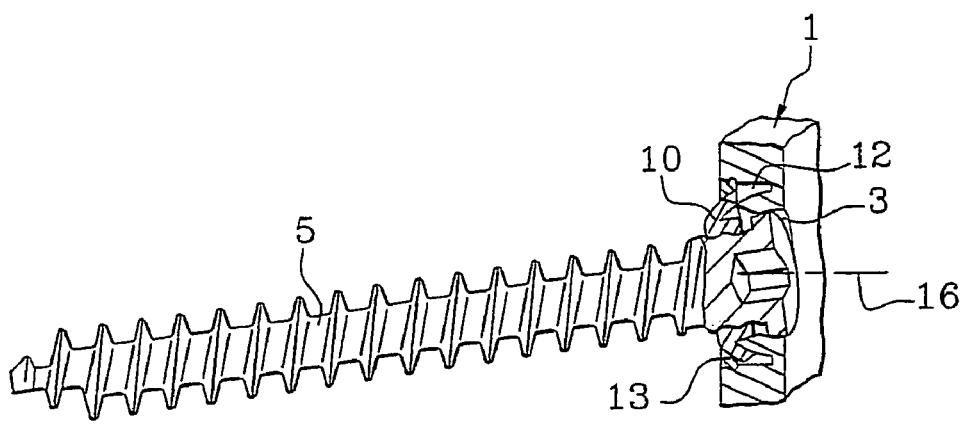
FIG. 10 shows the same implant as FIG. 9 but upon complete tilting clamping, i.e. the screw forms an angle with the axis of the orifice of the support.

FIG. 10 represents the fastening screw 5 upon complete screwing in a configuration tilted relative to the axis 16 of the orifice 3.

This tilting possibility is due to the fact that the nut 10 has a degree of freedom in its reception housing 12. On the other hand, the spherical contact surfaces of the screw head/supporting plate and supporting plate/nut enable to obtain high clamping quality regardless of the admissible tilt of the axis of the screw 5 relative to the axis 16 of the orifice 3.

One may also provide a spherical contact surface between the nut 10 and the locking clip 13 for better guiding of the nut 10 when positioning the screw 5 when starting the screwing process.

The corresponding contact surfaces are detailed below in connection with the description of each constitutive part of the implant.

FIGS. 11 and 12 represent in detail the configuration of the circular orifice 3 and of the housing 12 which is laid out in the supporting structure 1, which housing 12 is intended to receive the nut 10 detailed on FIGS. 13 to 16. This nut 10 is held preferably by a locking clip detailed on FIGS. 17 to 19, which clip enables easier disassembly of the nut than when said nut is crimped in position.

As represented on FIGS. 11 and 12, the supporting plate 1 includes a spherical ring 312 formed of a first spherical crown 31 for contact with the screw head 6, and of a second spherical crown 32 for contact with the nut 10.

The peripheral portion 313 which extends between both spherical crowns 31 and 32, is of truncated form, with sufficient angle to allow movement of the nut 10 and hence of the screw 5 relative to the supporting part 1. This portion 313 may form a stop for the nut 10 and in particular for its shaft 100 as detailed below.

On the circular periphery of the housing 12, one may note the presence of a circular throat 33 intended for positioning and locking the retaining clip 13.

The means locking the rotation of the nut 10 with respect to the support 1 are formed of at least one toe or tang. FIG. 11 shows three tangs 34 distributed regularly in the bottom of the circular housing 12, between the periphery of said housing and the spherical crown 32. These tangs 34 co-operate with homologue female shapes detailed below, provided on the nut 10 for locking the latter in rotation.

As represented on FIGS. 13 to 16, the nut 10 has a spherical crown 35 intended for contact with the supporting structure 1 and in particular the spherical crown 32 of the ring 312. One may also provide an external spherical crown 36 intended for contact with the holding clip 13. Said spherical crowns 35, 36 are part of a spherical ring 356 connected to the lower periphery of a cylindrical shaft 100 serving as a nut, which shaft is fitted with the female thread 30.

The external peripheral surface of the shaft 100 is accommodated with a certain clearance in the truncated portion 313 of the support 1, so as not to alter the ball-joint spherical contacts between the nut 10 and said support.

The amplitude of the movement of the nut 10 with respect to the support 1 may be limited by the truncated portion 313 of said support, which acts as a stop for the shaft 100 of the nut 10.

The spherical surface 36 optimises the correct spatial positioning of the nut when introducing the screw 5. The degree of freedom of the nut 10 in its reception housing 12 enables self-centring of the fastening screw 5 and of the associated nut when fastening the implant.

Figure 13:
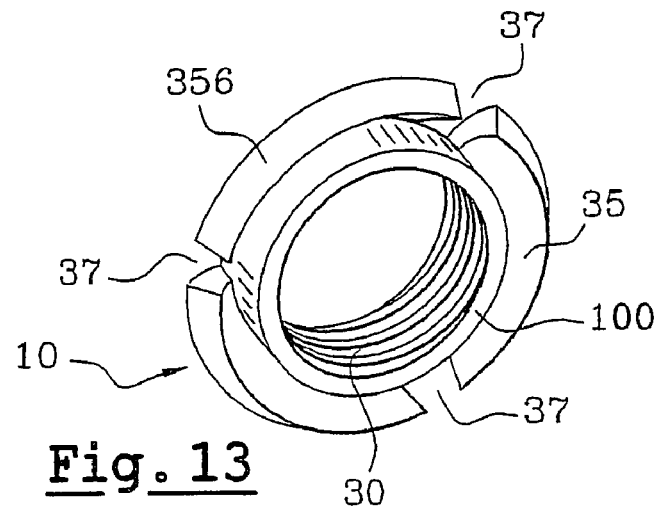
FIG. 13 is also a large-scale perspective view, of a nut for the implant illustrated on FIGS. 8 to 10.
Figure 14:
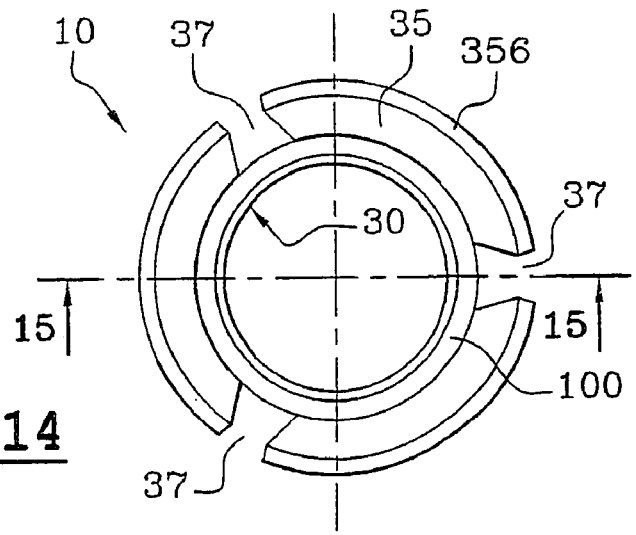
FIG. 14 is a view of the upperside of the nut illustrated on FIG. 13.
Figure 15:
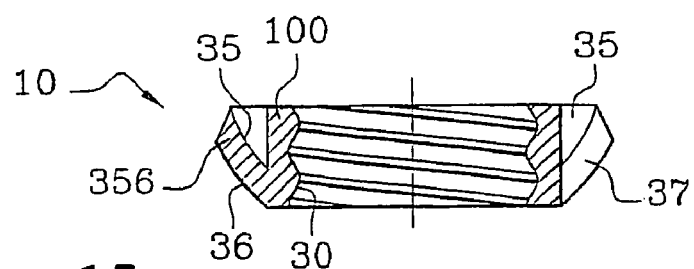
FIG. 15 is a diametrically sectional view according to 15-15 of FIG. 14.
Figure 16:
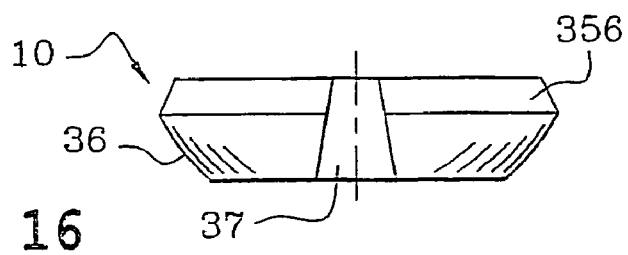
FIG. 16 is a lateral view of the nut illustrated on FIGS. 13 to 15.

On FIGS. 13 and 14, one may see the female shapes, aforementioned, in the form of cavities or notches 37 which are designed for co-operating with the tangs 34 of the supporting structure 1 in order to lock the nut 10 in rotation. The sides of these cavities or notches 37 may be parallel or slightly divergent, as illustrated on FIGS. 13, 14 and 15.

In the exemplary embodiment illustrated, the tangs 34 and the homologue notches 37 are three in number, laid out at 120° respectively in the bottom of the housing 12 of the supporting structure 1, and at the periphery of the nut 10. Cutting the spherical crown 356 using the notches 37 confers certain elasticity to the nut 10.

As represented on FIGS. 17 to 19, the clip 13 is in the form of a circular ring fitted with a slot 38 providing thereby certain radial elasticity. On its external periphery, this clip 13 is fitted with a peripheral rib or emboss 39 which may be imbedded in the circular throat 33 of the housing 12 laid out in the support 1. Imbedding the clip 13 on the supporting structure 1 is made possible by the presence of the slot 38. The clip 13 is sized for holding the nut 10 in the housing 12.

The clip 13 is also fitted internally with a spherical crown 40 able to co-operate with the corresponding spherical crown 36 provided on the nut 10.

As mentioned before, upon complete screwing of the fastening screw 5, the different spherical crowns: —7 on the head 6 of the screw 5, —31 and 32 on the support 1, and —35 and 36 on the nut 10, are concentric; one the assembly complete, the corresponding centre 23 is positioned substantially in the plane of the upper surface of the supporting plate 1, as shown on FIG. 9.

The invention claimed is:

1. An implantable orthopedic device comprising:
    a) a supporting structure comprising:
        1) an upper face;
        2) a lower face; and
        3) at least one housing defined in the supporting structure, each said housing being partially defined by an upper spherical ring and partially closed by a lower holding element, each said upper spherical ring, housing, and lower holding element defining an orifice centered about an axis;
    b) at least one nut, made in one piece, comprising a female thread and a spherical contact surface, each said nut being shaped so as to be held within a respective one of the housings, between said upper spherical ring and said lower holding element;
    c) at least one fastening screw, each comprising:
        1) a threaded body sized so that the threaded body can pass through the orifice, the threaded body comprising a body thread proportioned to be able to cooperate with bone material; and
        2) a head sized to prevent the head from passing through the orifice, the head comprising:
            A) a collar having a peripheral contour in the form of a spherical contact surface; and
            B) head thread that is sized to engage the female thread of the nut, an outer diameter of the head thread being greater than or equal to an outer diameter of the body thread, the head thread being disposed between the collar and the body thread; and
    d) at least one relief and an adapted notch, one of which is disposed on the housing, another of which is disposed on the nut, the nut being, in the absence of engagement of the fastening screw, free to move within a predetermined tilting range to allow an axis of the female thread to be tilted with the respect to the axis of the upper spherical ring;
    wherein each said upper spherical ring comprises upper and lower spherical contact surfaces, having a same center, the upper and lower spherical contact surfaces being arranged to cooperate with said spherical contact surfaces of said screw head and said nut, respectively; and
    wherein each said spherical ring, nut, and fastening screw are designed so that each said fastening screw can be passed through a respective one of the orifices and threaded through a corresponding said nut so as to clamp the spherical ring between the nut and the screw head at a selected angle within the tilting range and while keeping contact between said corresponding spherical contact surfaces; and
    wherein the notch and relief are positioned and sized so that, even when the fastening screw is not engaged with the nut, the nut is locked in the housing to prevent rotation about an axis of the female thread.

2. The implantable device of claim 1, wherein the holding element comprises a clip that partially closes the housing.

3. The implantable device of claim 2, wherein the clip is an open circular loop that comprises a snapon groove cooperating with a throat in the housing.

4. The implantable device of claim 1, wherein the cylindrical contact surfaces between the screw head and the supporting structure, and the cylindrical contact surfaces between the supporting structure and the nut have a same orientation axis.

5. The implantable device of claim 4, wherein the cylindrical contact surfaces are arranged so that the orientation axis is situated in a vicinity of an upper plane of the supporting structure.

6. The implantable orthopedic device of claim 1, wherein the upper spherical ring extends inward from the upper face of the supporting structure.

* * * * *